United States Patent
Kim et al.

(10) Patent No.: US 10,501,403 B2
(45) Date of Patent: Dec. 10, 2019

(54) METHOD FOR PREPARATION OF (S)-N1-(2-AMINOETHYL)-3-(4-ALKOXYPHENYL)PROPANE-1,2-DIAMINE TRIHYDROCHLORIDE

(71) Applicant: ST PHARM CO., LTD., Gyeonggi-do (KR)

(72) Inventors: Yeong Hun Kim, Gyeonggi-do (KR); Hyun Woo Baek, Gyeonggi-do (KR); Hyeon Jin Lee, Gyeonggi-do (KR); Sang Kyu Kang, Gyeonggi-do (KR); Sun Ki Chang, Gyeonggi-do (KR); Geun Jho Lim, Seoul (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 0 days.

(21) Appl. No.: 16/347,514

(22) PCT Filed: Nov. 3, 2017

(86) PCT No.: PCT/KR2017/012389
§ 371 (c)(1),
(2) Date: May 3, 2019

(87) PCT Pub. No.: WO2018/084625
PCT Pub. Date: May 11, 2018

(65) Prior Publication Data
US 2019/0284126 A1   Sep. 19, 2019

(30) Foreign Application Priority Data
Nov. 4, 2016   (KR) .......................... 10-2016-0146850

(51) Int. Cl.
*C07C 211/27* (2006.01)
*C07C 209/22* (2006.01)
*C07C 269/06* (2006.01)
*C07C 271/20* (2006.01)
*C07C 217/62* (2006.01)

(52) U.S. Cl.
CPC .......... *C07C 211/27* (2013.01); *C07C 209/22* (2013.01); *C07C 217/62* (2013.01); *C07C 269/06* (2013.01); *C07C 271/20* (2013.01)

(58) Field of Classification Search
CPC ... C07C 211/27; C07C 209/22; C07C 217/62; C07C 269/06; C07C 271/20; C07C 303/30; C07C 309/66; C07C 2601/14; C07C 2601/08
See application file for complete search history.

(56) References Cited

FOREIGN PATENT DOCUMENTS

| CN | 101007775 A | 8/2007 |
|---|---|---|
| CN | 103896788 A | 7/2014 |
| CN | 104761461 A | 7/2015 |
| CN | 105001118 A | 10/2015 |
| KR | 10-1152899 | 6/2012 |
| WO | WO-2017208258 A1 * 12/2017 ........... C07C 271/16 |

OTHER PUBLICATIONS

Epstein, "Alkoxyphenyl N-Substituted aminopropanols." Journal of the Americacan Chemical Society 81:6207-6209 (1959).
White et al., "Cyclic sulfamate from N-substituted 2-amino-3-phenyl-1-propanol and its nucleophilic reactions." The Journal of Organic Chemistry 56:3177-3178 (1991).
Sabitha et al, "Highly regioselective ring opening of epoxides and aziridines using cerium(III) chloride," Tetrahedron Letters 42:3955-3958 (2001).

* cited by examiner

*Primary Examiner* — Jafar F Parsa
(74) *Attorney, Agent, or Firm* — Cooley LLP

(57) ABSTRACT

The present invention relates to a novel method for preparing (S)—N$^1$-(2-aminoethyl)-3-(4-alkoxyphenyl)propane-1,2-diamine trihydrochloride.

20 Claims, No Drawings

METHOD FOR PREPARATION OF (S)-N1-(2-AMINOETHYL)-3-(4-ALKOXYPHENYL)PROPANE-1,2-DIAMINE TRIHYDROCHLORIDE

CROSS-REFERENCE TO RELATED APPLICATIONS

This application is a U.S. national phase application of International PCT Patent Application No. PCT/KR2017/012389, which was filed on Nov. 3, 2017, which claims priority to Korean Patent Application No. 10-2016-0146850, filed Nov. 4, 2016. These applications are incorporated herein by reference in their entireties.

TECHNICAL FIELD

The present invention relates to a novel method for preparing (S)—$N^1$-(2-aminoethyl)-3-(4-alkoxyphenyl)propane-1,2-diamine trihydrochloride.

BACKGROUND ART

EOVIST® is a paramagnetic contrast agent for magnetic resonance imaging (MRI), and is used for MRI of blood vessels, tissues, and other non-bony tissues, and particularly usefully, for diagnosis of an abnormality in the liver tissue. EOVIST® includes gadoxetate disodium as an active pharmaceutical ingredient, having a molecular weight of 725.72, an empirical formula of $GdC_{23}H_{28}N_3O_{11}Na_2$, and a structural formula of gadolinium (4S)-4-(4-ethoxybenzyl)-3,6,9-tris(carboxylatomethyl)-3,6,9-triazaundecanoic acid disodium salt. Gadoxetate disodium has a structure of Formula (a) below in an aqueous solution.

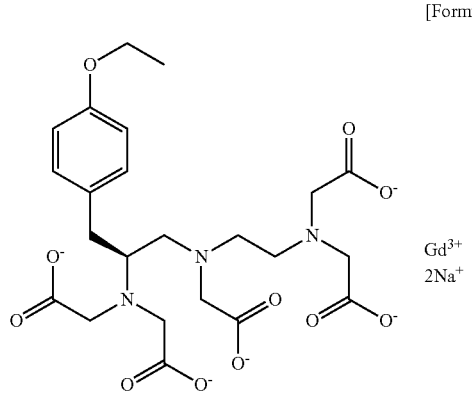

[Formula (a)]

In order to synthesize the compound of Formula (a), a method for synthesizing (S)-2,2'-(2-((2-(bis(carboxymethyl)amino)-3-(4-ethoxyphenyl)propyl)(carboxymethyl)amino)ethylazanediyl)diacetic acid, which is an intermediate from (S)—$N^1$-(2-aminoethyl)-3-(4-ethoxyphenyl)propane-1,2-diamine, is disclosed in Chinese patent application publication No. CN104761461. However, there is no reference disclosing a method for preparing (S)—$N^1$-(2-aminoethyl)-3-(4-ethoxyphenyl)propane-1,2-diamine trihydrochloride, which is used as a reactant, from 4-bromophenetole, which is a commercially available compound.

DISCLOSURE

Technical Problem

The present inventors have long conducted research to find a method for providing (S)—$N^1$-(2-aminoethyl)-3-(4-alkoxyphenyl)propane-1,2-diamine trihydrochloride as an intermediate that can be used for the preparation of gadoxetate disodium, and as a result, they have confirmed that a series of processes including Grignard coupling from 1-halo-4-ethoxybenzene is an economic and simple process enabling efficient mass production of (S)—$N^1$-(2-aminoethyl)-3-(4-alkoxyphenyl)propane-1,2-diamine trihydrochloride, thereby completing the present invention.

Technical Solution

To achieve the objective, an exemplary embodiment of the present invention provides a method for preparing (S)—$N^1$-(2-aminoethyl)-3-(4-alkoxyphenyl)propane-1,2-diamine trihydrochloride, comprising the following steps: (1) preparing a compound of Formula 2 by Grignard coupling of a compound of Formula 1; (2) preparing a compound of Formula 3 by azide substitution of the compound of Formula 2 in the reaction with sodium azide; (3) preparing an aziridine derivative having a protected amino group of Formula 4 by cyclization of the compound of Formula 3 using triphenylphosphine; (4) preparing a compound of Formula 5 by ring opening of the compound of Formula 4; and (5) preparing a compound of Formula 6 by a reaction for removing the amino-protect group of the compound of Formula 5:

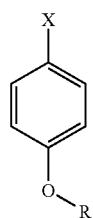

[Formula 1]

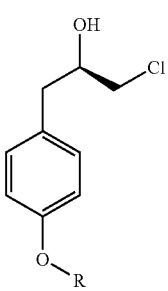

[Formula 2]

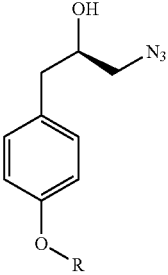

[Formula 3]

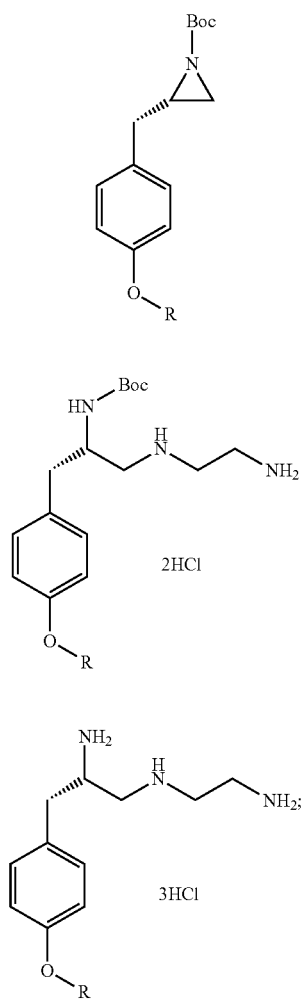

[Formula 4]

[Formula 5]

[Formula 6]

wherein X is bromo or chloro, and

R is 01-6 alkyl.

For example, X may be bromo.

For example, R may be ethyl.

Conventionally, methods for preparing (S)—N$^1$-(2-aminoethyl)-3-(4-alkoxyphenyl)propane-1,2-diamine trihydrochloride have been performed using a compound including a hydroxy group and further including a step for introducing alkoxy, e.g., ethoxy, and had inconveniences such as requiring further hydrogenation using Pd/C to remove unnecessary functional groups. Accordingly, the present invention is technically characterized by streamlining a method for preparing (S)—N$^1$-(2-aminoethyl)-3-(4-alkoxyphenyl)propane-1,2-diamine trihydrochloride by using an easily accessible simple compound which is commercially available and minimizing such unnecessary processes.

Specifically, step (1) can be performed by Grignard coupling. For example, step (1) can be performed by step (1-1) of preparing a Grignard compound by reacting the compound of Formula 1 with a metallic or organometallic compound; and step (1-2) of reacting the Grignard compound with a compound of Formula 7:

[Formula 7]

The metallic or organometallic compound of step (1-1) may be any substance known in the art that can be prepared as a Grignard compound, without limitation. For example, the compound may be magnesium, but is not limited thereto.

A solvent in step (1) may be any organic solvents used commonly in Grignard coupling, without limitation. For example, the solvent may be tetrahydrofuran (THF), 1,4-dioxane, diethylether, or a mixture thereof, specifically, tetrahydrofuran (THF), but is not limited thereto.

Specifically, step (1-1) may be performed at a temperature of 20° C. to 60° C. Step (1-1) is to prepare a Grignard compound by reacting a halogen compound with metal, and performing the step at a high temperature may cause undesirable side reactions. Accordingly, after slowly adding a reactant at a low temperature of 20° C. to 30° C., the temperature may be increased for the reaction, but a method for adjusting the temperature is not limited thereto.

Meanwhile, step (1-2) may be performed at a temperature of −20° C. to 30° C., and specifically 0° C. to 20° C., but is not limited thereto. A reactant used in (1-2) is highly reactive, and accordingly, it is desirable that the reaction is performed at a low temperature. For example, adding a reactant at a temperature as low as −5° C. may block reactions in an undesirable direction.

Step (1-2) may be performed by further comprising a Lewis acid as a catalyst. Unlimited examples of the Lewis acid may include $CuBrS(CH_3)_2$, CuI, and $CuCl_2$, and specifically may be CuI, but the Lewis acid is not limited thereto.

After step (1), at least one step of isolating, purifying, and concentrating the prepared compound may be further performed, but is not limited thereto. For example, according to an exemplary embodiment, the prepared compound of step (1) is extracted using an organic solvent, and the obtained organic layer is washed using an aqueous solution of EDTA and a 20% aqueous solution of sodium chloride, followed by drying over sodium sulfate and filtration. The filtrate is concentrated to obtain the resulting compound.

In the preparation method of the present invention, step (2) may be performed to substitute a halogen obtained by step (1), e.g., a chloro group of a compound including chloro, with azide.

A solvent in step (2) may be any organic solvent used commonly in azide substitution, without limitation. For example, the solvent may be dimethylformamide, but is not limited thereto.

Meanwhile, step (2) may be performed at a temperature of 70° C. to 100° C., e.g., 80° C. to 90° C. or 80° C. to 85° C., but is not limited thereto.

After step (2), at least one step of isolating, purifying, and concentrating the prepared compound may be further performed, but is not limited thereto. For example, according to an exemplary embodiment, the prepared compound of step (2) is extracted using an organic solvent, and the obtained organic layer is washed using an aqueous solution of hydrochloric acid, a 5% aqueous sodium bicarbonate solution, and a 10% aqueous sodium chloride solution, followed by drying over sodium sulfate and filtration. The filtrate is concentrated to obtain the resulting compound.

Specifically, step (3) can be performed by step (3-1) of forming an aziridinyl group of Formula 3-1 by cyclization by triphenylphosphine; and step (3-2) of introducing a protecting group to an amino group by reacting the compound including the aziridinyl group obtained in step (3-1) with di-tert-butyl dicarbonate:

[Formula 3-1]

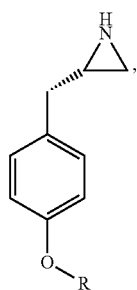

wherein R is the same as previously defined.

For example, R may be ethyl.

That is, after forming an aziridinyl group, which is a ring structure including an amino group, by condensing hydroxy and azide groups of a compound of Formula 3, a tert-butyl protecting group may be introduced to an amino group of the aziridinyl group.

Step (3-2) may be performed by further comprising a catalyst, such as 4-dimethylaminopyridine and iodine ($I_2$), or an alkaline substance, such as triethanolamide (TEA), N,N-diisopropylethylamine (DIEA), and $NaHCO_3$, but is not limited thereto.

For example, step (3) may be performed using acetonitrile, toluene, or a mixture thereof as a solvent. Specifically, the solvent may be acetonitrile, but is not limited thereto.

Additionally, step (3-1) may be performed at a temperature of 55° C. to 70° C., specifically, 60° C. to 65° C., but is not limited thereto.

Further, step (3-2) may be performed at a temperature of 20° C. to 30° C., specifically, 20° C. to 25° C., but is not limited thereto.

The ring opening of step (4) may be performed using acetonitrile, tetrahydrofuran, toluene, or a mixture thereof as a solvent. Specifically, the solvent may be acetonitrile, but is not limited thereto.

Additionally, step (4) may be performed at a temperature of 45° C. to 55° C., specifically, 50° C. to 52° C., but is not limited thereto.

Meanwhile, step (5) of removing the amino-protecting group may be performed using trifluoroacetic acid, hydrochloric acid, methanolic hydrochloric acid, or a mixture thereof. Specifically, methanolic hydrochloric acid may be used, but is not limited thereto.

Step (5) may be performed using methanol, dichloromethane, tetrahydrofuran, or a mixture thereof, specifically methanol, as a solvent.

Meanwhile, in step (5), methanolic hydrochloric acid may be provided by mixing acetyl chloride in a methanol solvent, but is not limited thereto.

Further, step (5) may be performed at a temperature of 45° C. to 55° C., specifically, 50° C. to 52° C., but is not limited thereto.

Further, steps (4) and (5) may further comprise either step (4-1) or (5-1), respectively, for crystallizing the prepared compounds, or both steps, after steps (4) and (5) are independently completed.

For example, step (4-1) may be performed using ethanol, ethyl acetate, or a mixture thereof as a solvent. Specifically, a compound of Formula 5 may be crystallized using a mixture of ethanol and ethyl acetate as a solvent, but is not limited thereto.

Meanwhile, step (5-1) may be performed using methanol, acetone, methyl tert-butyl ether, or a mixture thereof as a solvent. Specifically, a compound of Formula 6 may be crystallized using methyl tert-butyl ether as a solvent, but is not limited thereto.

Advantageous Effects

The preparation method of the present invention uses reasonably priced raw materials and simple reaction processes, and accordingly enables efficient and economic production of (S)—$N^1$-(2-aminoethyl)-3-(4-alkoxyphenyl) propane-1,2-diamine trihydrochloride, and can therefore be usefully applied to commercialized mass production thereof.

MODE FOR INVENTION

Hereinafter, the present invention will be described in detail with accompanying exemplary embodiments. However, the exemplary embodiments disclosed herein are only for illustrative purposes and should not be construed as limiting the scope of the present invention.

Hereinafter, samples and solvents without a specific disclosure were purchased from Sigma-Aldrich Korea, and $^1$H-NMR spectroscopy was performed using a Bruker 400 MHz NMR spectrometer.

According to the reaction formula below, Examples 1 to 5 were conducted.

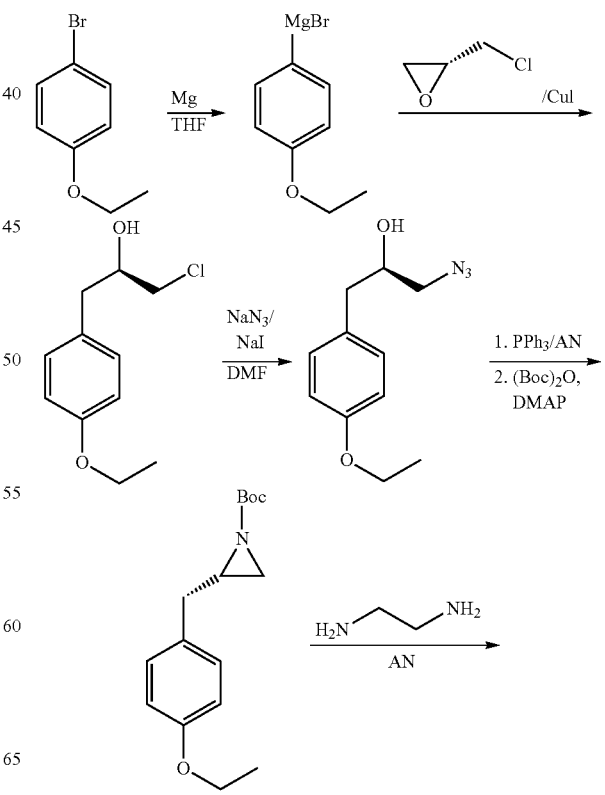

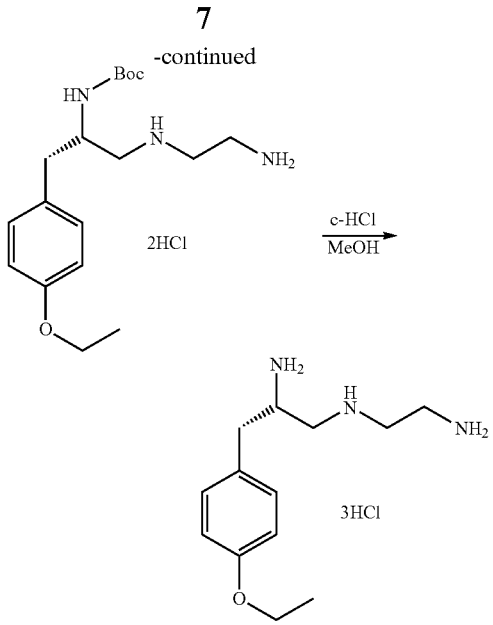

Example 1: Preparation of (R)-1-chloro-3-(4-ethoxyphenyl)propane-2-ol

In a reactor substituted with a nitrogen atmosphere, magnesium (14.50 g, 596.84 mmol) was added to 600 mL of THF, and the mixture was stirred to dissolve. While maintaining the temperature at 20° C. to 30° C., 4-bromophenetole (120.0 g, 596.84 mmol) was slowly added. After the completion of the addition, the temperature was raised to 60° C., and the mixture was stirred for 2 hours, followed by cooling to −5° C., adding copper iodide (0.76 g, 2.98 mmol), and stirring the mixture for an additional 30 minutes. Thereafter, (R)-epichlorohydrin (49.70 g, 537.15 mmol) was slowly added, and the mixture was stirred at room temperature for 1 hour. After completion of the reaction, the temperature was reduced to 5° C., and aqueous hydrochloride acid (3 M, 600 mL) and isopropyl ether (360 mL) were added to separate into layers. The organic layer was washed twice with a 10% aqueous EDTA solution (480 mL) and a 20% aqueous sodium chloride solution (240 mL), dried over sodium sulfate, and the mixture was filtered. The filtrate was concentrated to obtain the title compound, (R)-1-chloro-3-(4-ethoxyphenyl)propane-2-ol (123.2 g, 100% yield).

$^1$H-NMR (CDCl$_3$, 400 MHz): δ (ppm) 1.41 (t, 3H), 2.17 (d, 1H), 2.83 (d, 2H), 3.49-3.61 (m, 2H), 4.00-4.04 (m, 3H), 6.85 (d, 2H), 7.14 (d, 2H).

Example 2: Preparation of (R)-1-azido-3-(4-ethoxyphenyl)propane-2-ol (R)-1-Chloro-3-(4-ethoxyphenyl)propane-2-ol (115.33 g, 537.15 mmol) prepared in Example 1 above was added to 580 mL of dimethylformamide, and the mixture was stirred to dissolve, followed by addition of sodium iodide (8.05 g, 53.72 mmol) and sodium azide (69.85 g, 1074.39 mmol) thereto. The temperature inside the reactor was raised to 85° C., and the mixture was stirred for 16 hours. After the completion of the reaction, the mixture was cooled to room temperature, and 580 mL of purified water and 580 mL of isopropyl ether were added to separate into layers. And then, the obtained water layer was further extracted with isopropyl ether (190 mL) twice. The recovered organic layer was washed with aqueous hydrochloric acid (1 M, 580 mL), a 5% aqueous sodium bicarbonate solution (580 mL), and a 10% aqueous sodium chloride solution (580 mL), dried over sodium sulfate, and the mixture was filtered. The filtrate was concentrated to obtain the title compound, (R)-1-azido-3-(4-ethoxyphenyl)propane-2-ol (113.5 g, 95.5% yield).

$^1$H-NMR (CDCl$_3$, 400 MHz): δ (ppm) 1.41 (t, 3H), 1.97 (d, 1H), 2.71-2.79 (m, 2H), 3.28 (dd, 1H), 3.38 (dd, 1H), 3.94-4.01 (m, 1H), 4.04 (q, 2H), 6.86 (d, 2H), 7.10 (d, 2H).

Example 3: Preparation of (S)-tert-butyl 2-(4-ethyoxybenzyl)aziridine-1-carboxylate In a reactor substituted with a nitrogen atmosphere, (R)-1-azido-3-(4-ethoxyphenyl)propane-2-ol (113.0 g, 510.71 mmol) prepared in Example 2 was added to acetonitrile (AN, 1130 mL), and the mixture was stirred, followed by addition of triphenylphosphine (PPh$_3$, 120.56 g, 459.64 mmol), stirring at room temperature for 2 hours, and refluxing for 4 hours. After completion of the reaction, the mixture was cooled to 20° C., and 4-dimethylaminopyridine (DMAP, 0.62 g, 122.17 mmol) and di-tert-butyl dicarbonate ((Boc)$_2$O, 100.32 g, 459.64 mmol) were slowly added, and the mixture was stirred for 30 minutes. After adding hydrogen peroxide (11.60 g, 102.14 mmol) to the mixture and stirring it for an additional 30 minutes, the resultant was concentrated, and the acetonitrile was removed. The obtained concentrate was charged with heptane (1130 mL), and the mixture was stirred at 20° C. to 25° C. for 30 minutes, followed by filtration of the resultant. The filtrate was concentrated to obtain the title compound, (S)-tert-butyl 2-(4-ethyoxybenzyl)aziridine-1-carboxylate (113.05 g, 93.9% yield).

$^1$H-NMR (CDCl$_3$, 400 MHz): b (ppm) 1.39-1.45 (m, 12H), 2.01 (d, 1H), 2.29 (d, 1H), 2.57-2.62 (m, 2H), 2.91 (q, 1H), 4.02 (q, 2H), 6.84 (d, 2H), 7.20 (d, 2H).

Example 4: Preparation of (S)-tert-butyl 1-(2-aminoethylamino)-3-(4-ethoxyphenyl)propane-2-ylcarbamate dihydrochloride (S)-tert-Butyl 2-(4-ethyoxybenzyl)aziridine-1-carboxylate (133.05 g, 479.70 mmol) prepared in Example 3 was added to acetonitrile (400 mL), and the mixture was stirred to dissolve, followed by addition of ethylenediamine (432.45 g, 7195.52 mmol) and stirring at 50° C. for 6 hours. After completion of the reaction, the resultant was concentrated and the inside temperature was reduced to 5° C., and an aqueous hydrochloric acid solution (2 M, 480 mL) and ethyl acetate (266 mL) were added to separate into layers. To the aqueous layer, a 50% aqueous sodium hydroxide solution (200 mL) was added, and the mixture was separated with ethyl acetate (530 mL). The organic layer was washed with 20% sodium chloride (266 mL), dried over sodium sulfate, and the mixture was filtered. The filtrate was dried under vacuum at 50° C. to obtain the title compound, (S)-tert-butyl 1-(2-aminoethylamino)-3-(4-ethoxyphenyl)propane-2-ylcarbamate dihydrochloride (135.5 g, 68.8% yield).

$^1$H-NMR (D$_2$O, 400 MHz): δ (ppm) 1.02 (s, 2H), 1.14 (s, 9H), 1.24 (t, 3H), 2.46 (dd, 1H), 2.82 (dd, 1H), 3.07 (t, 1H), 3.25-3.39 (m, 6H), 3.94-4.00 (m, 3H), 6.83 (d, 2H), 7.10 (d, 2H).

Example 5: Preparation of (S)—N$^1$-(2-aminoethyl)-3-(4-ethoxyphenyl)propane-1,2-diamine trihydrochloride In a reactor, methanol (950 mL) and acetyl chloride (77.75 g, 990.55 mmol) were added, and the mixture was stirred to dissolve. To the solution, (S)-tert-butyl 1-(2-aminoethylamino)-3-(4-ethoxyphenyl)propane-2-ylcarbamate dihydrochloride (135.5 g, 330.18 mmol) prepared in Example 4 was added, and the mixture was stirred at 50° C. for 1 hour. After completion of the reaction, methyl tert-butyl ether (950 mL) was added, and the mixture was crystallized and filtered. The obtained crystals were dried under vacuum at 50° C. to obtain the title compound, (S)—N$^1$-(2-aminoethyl)-3-(4-ethoxyphenyl)propane-1,2-diamine trihydrochloride (105.2 g, 99.8% yield).

$^1$H-NMR (D$_2$O, 400 MHz): δ (ppm) 1.38 (t, 3H), 3.00 (dd, 1H), 3.17 (dd, 1H), 3.43-3.58 (m, 6H), 3.94-4.01 (m, 1H), 4.13 (q, 2H), 7.03 (d, 2H), 7.31 (d, 2H).

The invention claimed is:
1. A method for preparing (S)—N$^1$-(2-aminoethyl)-3-(4-alkoxyphenyl)propane-1,2-diamine trihydrochloride, comprising the following steps:
   (1) preparing a compound of Formula 2 by Grignard coupling of a compound of Formula 1;
   (2) preparing a compound of Formula 3 by azide substitution of the compound of Formula 2 in a reaction with sodium azide;
   (3) preparing an aziridine derivative of Formula 4 having an amino group protected by an amino-protecting group by cyclization of the compound of Formula 3 using triphenylphosphine;
   (4) preparing a compound of Formula 5 by ring opening of the compound of Formula 4;
   (5) preparing a compound of Formula 6 by a reaction for removing the amino-protecting group of the compound of Formula 5:

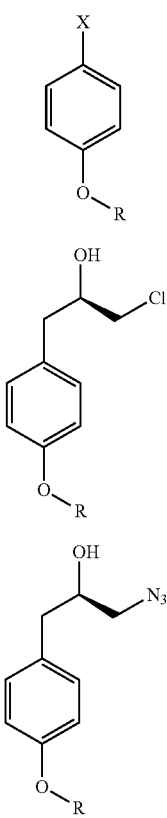

[Formula 1]

[Formula 2]

[Formula 3]

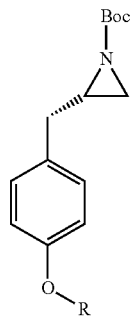

[Formula 4]

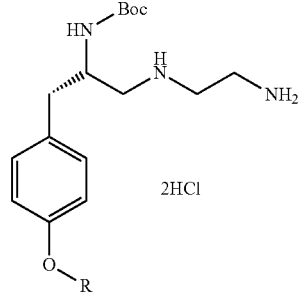

[Formula 5]

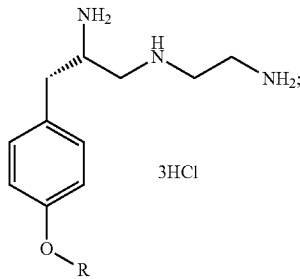

[Formula 6]

wherein X is bromo or chloro, and
R is C$_{1-6}$ alkyl.

2. The method of claim 1, wherein step (1) comprises the following steps:
   (1-1) preparing a Grignard compound by reacting the compound of Formula 1 with a metallic or organometallic compound; and
   (1-2) reacting the Grignard compound with a compound of Formula 7:

[Formula 7]

3. The method of claim 1, wherein step (1) is performed using tetrahydrofuran (THF), 1,4-dioxane, diethylether, or a mixture thereof as a solvent.

4. The method of claim 2, wherein step (1-1) is performed at a temperature of 20° C. to 60° C.

5. The method of claim 2, wherein step (1-2) is performed at a temperature of −20° C. to 30° C.

6. The method of claim 2, wherein step (1-2) is performed by further comprising a Lewis acid.

7. The method of claim 1, wherein step (2) is performed using dimethylformamide as a solvent.

8. The method of claim 1, wherein step (2) is performed at a temperature of 70° C. to 100° C.

9. The method of claim 1, wherein step (3) comprises the following steps:
- (3-1) forming an aziridinyl group of Formula 3-1 by cyclization by triphenylphosphine; and
- (3-2) introducing a protecting group to an amino group by reacting the compound including the aziridinyl group obtained by step (3-1) with di-tert-butyl dicarbonate:

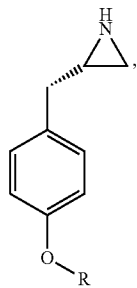

[Formula 3-1]

wherein R is the same as defined in claim 1.

10. The method of claim 9, wherein step (3-2) is performed by further comprising a catalyst selected from 4-dimethylaminopyridine and iodine (I₂), or an alkaline substance selected from triethanolamide (TEA), N,N-diisopropylethylamine (DIEA), and NaHCO₃.

11. The method of claim 1, wherein step (3) is performed using acetonitrile, toluene, or a mixture thereof as a solvent.

12. The method of claim 9, wherein step (3-1) is performed at a temperature of 55° C. to 70° C.

13. The method of claim 9, wherein step (3-2) is performed at a temperature of 20° C. to 30° C.

14. The method of claim 1, wherein step (4) is performed using acetonitrile, tetrahydrofuran, toluene, or a mixture thereof as a solvent.

15. The method of claim 1, wherein step (4) is performed at a temperature of 45° C. to 55° C.

16. The method of claim 1, wherein the reaction of step (5) is performed with trifluoroacetic acid, hydrochloric acid, methanolic hydrochloric acid, or a mixture thereof.

17. The method of claim 1, wherein step (5) is performed using methanol, dichloromethane, tetrahydrofuran, or a mixture thereof as a solvent.

18. The method of claim 1, wherein the reaction of step (5) is performed with acetyl chloride in a methanol solvent.

19. The method of claim 1, wherein step (5) is performed at a temperature of 45° C. to 55° C.

20. The method of claim 1, wherein steps (4) and (5) further comprise either step (4-1) or (5-1), respectively, for independently crystallizing the prepared compounds, or both steps.

* * * * *